(12) United States Patent
Sundaresan et al.

(10) Patent No.: US 10,218,791 B2
(45) Date of Patent: Feb. 26, 2019

(54) SYSTEMS AND METHODS FOR NETWORKED SENSOR NODES

(71) Applicant: General Electric Company, Schenectady, NY (US)

(72) Inventors: Krishnakumar Sundaresan, Clifton Park, NY (US); Radislav Alexandrovich Potyrailo, Niskayuna, NY (US); Feng Chen, Niskayuna, NY (US); Emad Andarawis Andarawis, Ballston Lake, NY (US); S M Shajedul Hasan, Rexford, NY (US)

(73) Assignee: General Electric Company, Schenectady, NY (US)

( * ) Notice: Subject to any disclaimer, the term of this patent is extended or adjusted under 35 U.S.C. 154(b) by 381 days.

(21) Appl. No.: 14/982,996

(22) Filed: Dec. 29, 2015

(65) Prior Publication Data

US 2017/0187541 A1   Jun. 29, 2017

(51) Int. Cl.
*H04L 1/00* (2006.01)
*H04L 29/08* (2006.01)
*G01R 27/02* (2006.01)

(52) U.S. Cl.
CPC .............. *H04L 67/12* (2013.01); *G01R 27/02* (2013.01)

(58) Field of Classification Search
CPC .......... H04L 67/12; G01R 27/02; G01R 27/28
See application file for complete search history.

(56) References Cited

U.S. PATENT DOCUMENTS

| 7,526,944 B2 | 5/2009 | Sabata et al. |
| 8,111,170 B2 | 2/2012 | Wilson et al. |

(Continued)

FOREIGN PATENT DOCUMENTS

| CN | 201982973 U | 9/2011 |
| CN | 204044102 U | 12/2014 |
| EP | 2752525 A1 | 7/2014 |

OTHER PUBLICATIONS

Jun et al., "A hydrogen leakage detection system using self-powered wireless hydrogen sensor nodes", Solid-State Electronics, vol. 51, Issue: 7, pp. 1018-1022, Jul. 2007.

(Continued)

*Primary Examiner* — Jeff W Natalini
(74) *Attorney, Agent, or Firm* — Mintz Levin Cohn Ferris Glovsky and Popeo, P.C.

(57) ABSTRACT

A sensor assembly includes an impedance sensor element, an impedance sensor reader and a communications module. The communications module is configured to communicate with a remote computing device. The impedance sensor reader is coupled to the impedance sensor element. The impedance sensor reader includes a synthesizer and a detector. The synthesizer is configured to output an excitation signal having known values for a plurality of signal characteristics to the impedance sensor element and to generate the excitation signal based on a plurality of direct digital synthesizer (DDS) coefficients received from the remote computing device through the communications module. The detector is coupled to the impedance sensor element and configured to detect a response of the impedance sensor element to the excitation signal and determine an impedance of the impedance sensor element based at least in part on the response of the impedance sensor element to the excitation signal.

14 Claims, 9 Drawing Sheets

(56) References Cited

U.S. PATENT DOCUMENTS

| | | | |
|---|---|---|---|
| 8,215,164 B1 | 7/2012 | Hussain et al. | |
| 2011/0190987 A1* | 8/2011 | Kincaid | B60R 21/00 |
| | | | 701/45 |
| 2012/0068827 A1 | 3/2012 | Yi et al. | |
| 2012/0256646 A1* | 10/2012 | Ginther | H04R 29/00 |
| | | | 324/686 |
| 2013/0271126 A1* | 10/2013 | Griswold | G01R 33/243 |
| | | | 324/301 |
| 2014/0095102 A1* | 4/2014 | Potyrailo | G01R 27/28 |
| | | | 702/127 |
| 2016/0091408 A1* | 3/2016 | Xiang | G01N 15/05 |
| | | | 324/693 |
| 2016/0334353 A1* | 11/2016 | Potyrailo | G01N 27/125 |

OTHER PUBLICATIONS

Vyas et al., "Inkjet Printed, Self Powered, Wireless Sensors for Environmental, Gas, and Authentication-Based Sensing", Sensors Journal, IEEE, vol. 11, Issue: 12, pp. 3139-3152, Dec. 2011.

\* cited by examiner

SYSTEMS AND METHODS FOR NETWORKED SENSOR NODES

BACKGROUND

The field of this disclosure relates generally to networked sensor node, and more particularly, to systems and methods for self-powered networked sensor nodes.

Networked sensor nodes with chemical sensors can be deployed in a variety of environments for sensing contaminants and concentration of particles that need to be tracked in the environment. Some known systems use sensors that detect chemicals based on a change in impedance of the sensor. The impedance of such sensors varies as a function of the size and concentration of molecules adsorbed on the surface. To detect the presence and concentration of the target chemical(s), the sensor determines the impedance of the sensor using a known excitation signal. Generating the known excitation signal is often computationally intensive and requires significant processing and electrical power.

Some known networked sensor nodes would be useful for placement around gas well pads to detect gas leaks. The network of such sensors may be deployed to cover a wide area around a well, so that maps of the gas leaks over the entire site can be collected and location of thermogenic leaks may be triangulated. In such installations, providing utility grid connections for each sensor node may be impossible or impractical. Moreover, powering known sensors with a stored energy device, such as a battery, requires undesirable maintenance to periodically replace the batteries. Additionally, batteries and other localized power sources may not be able to provide sufficient power for some known sensors unless the power source is increased to an undesirably large size.

BRIEF DESCRIPTION

In one aspect, a sensor assembly includes an impedance sensor element, an impedance sensor reader and a communications module. The communications module is configured to communicate with a remote computing device. The impedance sensor reader is coupled to the impedance sensor element. The impedance sensor reader includes a synthesizer and a detector. The synthesizer is configured to output an excitation signal having known values for a plurality of signal characteristics to the impedance sensor element. The synthesizer is configured to generate the excitation signal based on a plurality of direct digital synthesizer (DDS) coefficients received from the remote computing device through the communications module. The detector is coupled to the impedance sensor element. The detector is configured to detect a response of the impedance sensor element to the excitation signal and determine an impedance of the impedance sensor element based at least in part on the response of the impedance sensor element to the excitation signal.

In another aspect, a sensor network or a "mesh network" includes a plurality of sensor assemblies and a remote computing device. Each sensor assembly includes an impedance sensor element coupled to an impedance sensor reader, and a communications module. The impedance sensor reader is configured to generate an excitation signal based on a plurality of direct digital synthesizer (DDS) coefficients and determine an impedance of the impedance sensor element based at least in part on a response of the impedance sensor element to the excitation signal. The computing device is communicatively coupled to at least one sensor assembly. The computing device includes a processor and a memory device. The memory device stores instructions to cause the computing device to determine a plurality of DDS coefficients for at least one sensor assembly and deliver the plurality of DDS coefficients to the at least one sensor assembly. The plurality of DDS coefficients are determined to produce the excitation signal in the at least one sensor assembly.

In a further aspect, a method of operating a sensor node including an impedance sensor element includes receiving, by the sensor node, a plurality of direct digital synthesizer (DDS) coefficients from a remote computing device. The sensor node stores the plurality of DDS coefficients in a memory device. The sensor node generates an excitation signal based on the plurality of DDS coefficients and a clock signal. The sensor node determines an impedance of the impedance sensor element based at least in part on the response of the impedance sensor element to the excitation signal.

DRAWINGS

These and other features, aspects, and advantages of the present disclosure will become better understood when the following detailed description is read with reference to the accompanying drawings in which like characters represent like parts throughout the drawings, wherein.

Figure 1:
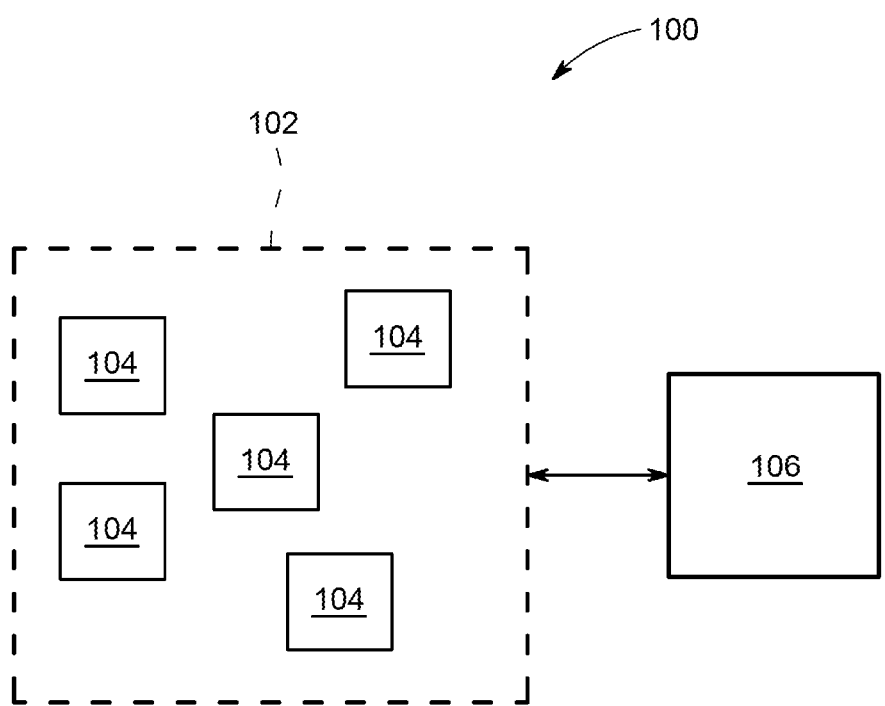
FIG. 1 is a block diagram of an exemplary sensor network.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit (ASIC), and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a compact disc—read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Embodiments of the present disclosure relate to networked sensor nodes, and more particularly, to self-powered networked sensor nodes. The sensor nodes described herein determine an impedance of an impedance sensor element using a predetermined input signal generated using direct digital synthesis (DDS). The DDS coefficients for the sensor nodes are calculated by a remote computing device and transmitted to each node to reduce the computational and electric load of sensor nodes. Moreover, various other power saving techniques are implemented in the sensor nodes to further reduce the power requirements of the sensor nodes. These relatively low power sensor nodes are self-powered by a localized power source, such as a solar panel and a rechargeable battery.

As used herein, the term "impedance sensor" or "impedance sensor element" means a sensor that has an equivalent circuit that includes at least one capacitor (C) component and at least one resistor (R) component. The R and C components in concert provide a RC circuit that has an impedance spectrum. The impedance spectrum of the RC circuit is affected by the changes in C and R components of the circuit. The "impedance sensor" may have an equivalent RC circuit that has more than one set of R and C components. For example, it may have two sets of R and C components or three sets of R and C components. The impedance spectrum of the RC circuit with more than one set of R and C components is affected by the changes in several C and several R components of the circuit.

In some embodiments, the impedance sensor may also have an inductance (L) component. Such an impedance sensor has an equivalent circuit that includes inductance (L) and at least one capacitor (C) and at least one resistor (R) components. When "impedance sensor element" includes at least one inductance (L), at least one capacitor (C), and at least one resistor (R) components, it may be referred to as a "resonant sensor element".

A sensor with an equivalent circuit that includes at least one inductance (L), at least one capacitor (C), and at least one resistor (R) components may operate (or "resonate") at one or more frequencies in a frequency range of analysis. A signal may be received from the sensor across the frequency range of analysis. The signal may be affected by the environment around the sensor. For example, the signal includes information about a sensor in contact with the fluid. One or more properties of the fluid may be determined based at least in part on the impedance spectra. The impedance sensors may be used to measure a variety of physical, chemical and/or biological parameters.

The sensor assembly (sometimes also referred to as a "sensor system" or a "sensor node") is intended to analyze an industrial fluid to determine one or more properties of the fluid such as external contaminants of the fluid and/or fluid aging based on the analyzed response of the impedance sensor. Nonlimiting examples of external contaminants are gases, particles, ions. Nonlimiting examples of aging are thermal degradation products of industrial fluid, oxidation degradation products of industrial fluid, ultraviolet degradation products of industrial fluid.

The sensor assembly may be a part of a mobile or stationary consumer electronics system or a part of a consumer system. Nonlimiting examples of the consumer electronics systems are smart phones, smart watches, tablets, textile-based wearable consumer electronics systems, and others known in the art.

Nonlimiting examples of the consumer systems are vehicles, automobiles, boats, furniture, homes, clothing, diapers and other components of baby care and other reusable and disposable consumer systems.

A communications module may be an integral part of the mobile or stationary consumer electronics system. The communications module may serve communications function for a variety of components of a mobile or stationary consumer electronics system. Nonlimiting examples of such components of a mobile or stationary consumer electronics system are telephone component, global positioning system (GPS) component, and impedance sensor component.

In an aspect, the industrial fluid of interest is at least one of ambient air at an industrial site, an oil, a fuel, a solvent, a solid, and a gas. Non-limiting examples of an industrial site include manufacturing facility, processing facility, disposal facility, industrial research facility, gas producing facility, oil producing facility, and others.

In some embodiments, a sensor according to this disclosure analyzes an industrial fluid, such as ambient air at an industrial site. Detection of methane and other gases may be performed using a sensor assembly. Detection of several gases or several other industrial fluids or their patterns or their signatures may be performed using a sensor assembly.

In some embodiments, a sensor assembly and/or a network of sensor assemblies or sensor nodes is performing monitoring of industrial process. Nonlimiting examples of industrial process include production of raw gas, material extraction, material transport, production of raw oil, operation of an internal combustion engine, operation of an oil-filled transformer, a chemical reaction process, a biological reaction process, purification and/or separation process, a catalytic process, a general combustion process, and other industrial processes.

Some embodiments of an impedance sensor or impedance sensor element of this disclosure includes at least two partially or fully independent outputs in response to an industrial fluid. Such a sensor is sometimes referred to as a "multivariable sensor". An example multivariable gas sensor includes a sensing material with diverse responses to different gases, a multivariable sensor element with different outputs to recognize these different responses, and data analytics to provide accurate gas quantitation based on the outputs. An example multivariable biological sensor includes a sensing material with diverse responses to different biological species, a multivariable sensor element with different outputs to recognize these different responses, and data analytics to provide accurate quantitation based on the outputs. An example multivariable physical sensor includes a multivariable sensor element with different outputs to different physical effects from the industrial fluid. Nonlimiting examples of such physical effects may be dielectric constant, conductivity, temperature, pressure of the industrial fluid.

The multivariable response of the sensor may be analyzed by multivariate analysis. Nonlimiting examples of multivariate analysis of multivariable response of the sensor may be Principal Components Analysis (PCA), Independent Component Analysis (ICA), Linear Discriminant Analysis (LDA), and Flexible Discriminant Analysis (FDA), Partial Least Squares (PLS), and many others known in the art.

FIG. 1 is a block diagram of a sensor network 100. Sensor network 100 includes a group 102 of sensor assemblies 104 and a remote computing device 106. Although five sensor assemblies 104 are shown in FIG. 1, group 102 may include more or fewer sensor assemblies 104.

In the exemplary embodiment, sensor assemblies 104 each include a chemical sensor such as an impedance sensor element (not shown in FIG. 1) to sense, for example, industrial fluid. Sensor assemblies 104 are in direct or indirect communication with remote computing device 106. In the exemplary embodiment, sensor assemblies 104 communicate using any suitable wireless communication protocol. In other embodiments, sensor assemblies 104 communicate using a wired communication protocol. Communication with remote computing device 106 allows sensor assemblies 104 to change data acquisition parameters for the impedance sensor element and to provide sensor data to remote computing device 106. The sensor data may be collected sensor data, data determined from collected sensor data, or both collected and determined sensor data. The collected sensor data includes the raw values received from the sensor. Determined sensor data may be calculated from the raw values received from the sensor, from the raw values received from more than one sensor, from other determined sensor data, or both. Sensor assemblies 104 may include sensors of the same kind or of different kinds. Sensors can be configured to sense same of different measurands including methane, carbon monoxide, hydrocarbons, temperature, humidity, and other environmental parameters.

In the exemplary embodiment, the chemical sensor is an impedance sensor element and the collected sensor data is a response of the impedance sensor element to a predetermined input signal (also referred to sometimes herein as an excitation signal and a known input signal). In the exemplary embodiment, the excitation signal is a sinusoidal signal with a known frequency and amplitude. The response of the impedance sensor element to the known input signal is used calculate the impedance of the impedance sensor element. The impedance of the impedance sensor element changes as a function of the size and concentration of molecules adsorbed on the surface of the impedance sensor element. A concentration of gas of interest in the environment (industrial fluid) around a particular one of sensor assemblies 104 is calculated by comparing the calculated impedance of the sensor assembly's impedance sensor element to an initial impedance of that impedance sensor element. In an exemplary embodiment, each sensor assembly 104 determines the impedance of its impedance sensor element and transmits the calculated impedance to remote computing device 106. In the exemplary embodiment, the chemical sensor is an impedance sensor element where the collected sensor data is a response of the impedance sensor element to a predetermined input signal.

Each sensor assembly 104 generates its own predetermined input signal in the exemplary embodiment. The signal is generated by direct digital synthesis (DDS) using a DDS synthesizer (not shown in FIG. 1). Thus, each sensor assembly is operable to know the specific characteristics, such as amplitude and frequency for example, of the predetermined input signal. DDS coefficients are used by the DDS synthesizer to generate the predetermined input signal. The DDS coefficients for each sensor assembly 104 are calculated by remote computing device 106 and transmitted to the sensor assemblies 104. In the exemplary embodiment, remote computing device 106 calculates separate DDS coefficients for each sensor assembly 104 and transmits the DDS coefficients to the particular sensor assembly 104 for which they were calculated. In some other embodiments, remote computing device 106 calculates a set of DDS coefficients to be used by more than one sensor assembly 104 (including possibly all sensor assemblies 104) and transmits the set of DDS coefficients to the sensor assemblies 104 for which they were calculated.

The DDS coefficients are calculated, in some embodiments, to account for one or more real world, operational characteristic of a sensor assembly 104. For example, if a sensor assembly 104, or a portion of the sensor assembly 104, is prone to second harmonic distortion, the DDS coefficients may be determined to account for and attempt to reduce the second harmonic distortion. The DDS coefficients may be predistorted based on the difference between an actual operational characteristic of a sensor assembly 104 and an ideal (or theoretical) operational characteristic of that sensor assembly 104. The DDS coefficients can be predistorted, for example, to account for the difference between ideal wires with no resistance or inductance and actual real world wires that have both resistance and inductance. This permits the sensor assembly 104 to treat wires (and other components and circuits) as ideal components, thereby simplifying the calculations to be performed by the sensor assembly 104. In some embodiments, remote computing device 106 relies on quarter wave symmetry of the predetermined input signal to permit reduction in the required DDS coefficients.

In the exemplary embodiment, sensor assemblies 104 are communicably coupled to each other to form a wireless mesh network. At least one of the sensor assemblies 104 is additionally coupled in wired or wireless communication with remote computing device 106. Communications from a sensor assembly 104 to remote computing device 106 may be passed through one or more other sensor assemblies 104 to reach remote computing device 106. Similarly, communications from remote computing device 106 may be passed through one or more other sensor assemblies 104 to reach the sensor assembly 104 that is the target of the communication. In other embodiments, each sensor assembly 104 is communicatively coupled to remote computing device 106, such as in a star network configuration, and communicates with remote computing device 106 without the assistance of other sensor assemblies 104. In still other embodiments, one or more of sensor assemblies 104 is coupled in communication with a gateway device (not shown) that is coupled in communication with remote computing device 106.

A user (not shown) may use remote computing device 106 to monitor any or all of sensor assemblies 104, the collected sensor data, and the determined sensor data. As described above, in some embodiments, remote computing device 106 receives the collected sensor data from sensor assemblies 104 and calculates the determined sensor data based on the collected sensor data. In some embodiments, remote computing device 106 is configured to generate an alert based on the collected sensor data, the determined sensor data, or a combination of the collected sensor data and the determined sensor data. The alert may be a human perceivable alert, such as an audible or visible alarm, or an alert that is not perceivable by humans, such as an alert directed at another computing device. The alert may be triggered, for example, when the impedance reported by one of the sensor assemblies 104 exceeds a threshold, when the change in the impedance of one of the sensor assemblies 104 exceeds a threshold, or when the determined data associated with one of the sensor assemblies 104 indicates a gas concentration or presence exceeding a threshold. Remote computing device 106 may be located any suitably distance from sensor assemblies 104. In an example embodiment, sensor assemblies 104 and remote computing device 106 are located around a natural gas well pad. In some other embodiments, sensor assemblies 104 are located around a natural gas well pad and remote computing device 106 is located at another location (such as in a building meters or kilometers away). Moreover, in some embodiments, remote computing device is located anywhere in the world and communicatively connected to sensor assemblies 104 by a communications network, such as the Internet.

Figure 2:
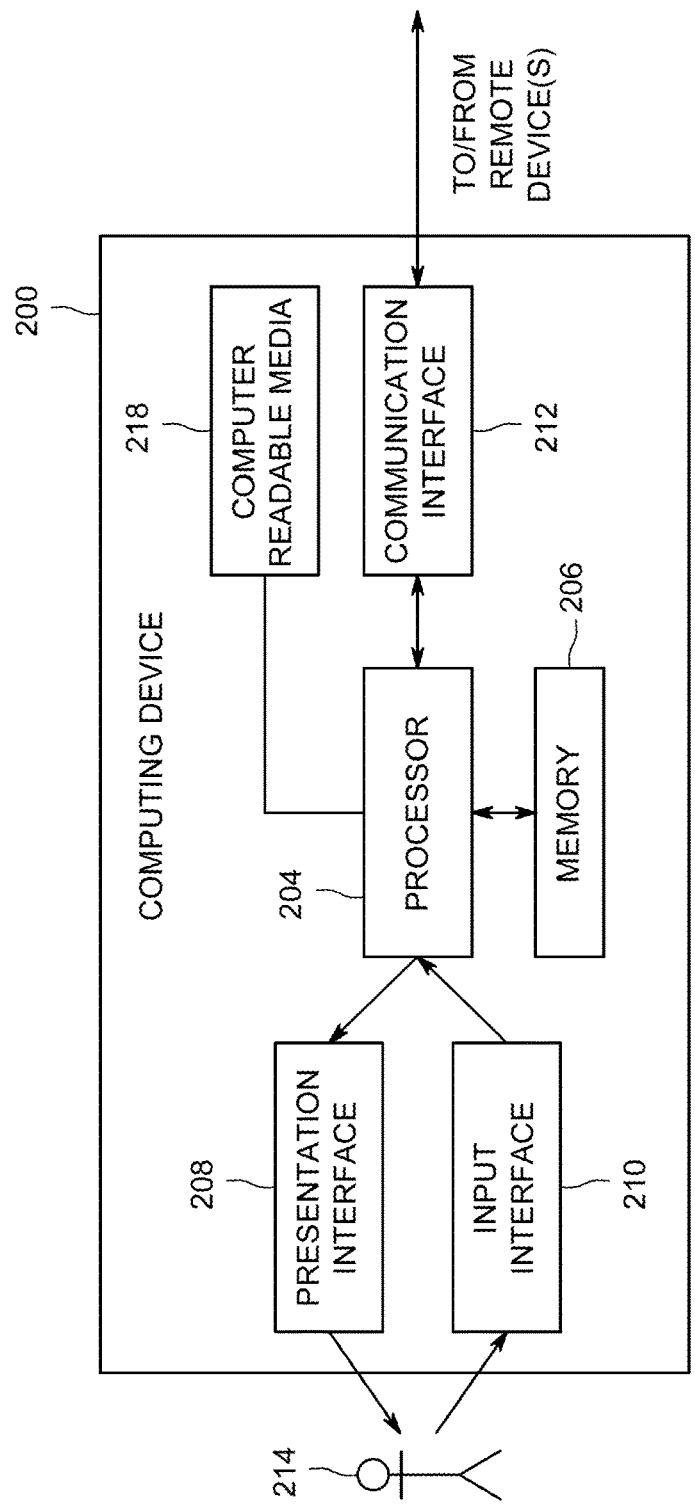
FIG. 2 is a block diagram of an exemplary computing device for use in the network shown in FIG. 1.

FIG. 2 is a block diagram of an exemplary computing device 200 that may be used in sensor network 100 (shown in FIG. 1) as remote computing device 106 (shown in FIG. 1), as part of sensor assemblies 104 (shown in FIG. 1), or both. In the exemplary embodiment, computing device 200 includes a memory 206 and a processor 204 that is coupled to memory 206 for executing programmed instructions. Processor 204 may include one or more processing units (e.g., in a multi-core configuration). Computing device 200 is programmable to perform one or more operations described herein by programming memory 206 and/or processor 204. For example, processor 204 may be programmed by encoding an operation as one or more executable instructions and providing the executable instructions in memory device 206. The executable instructions, when executed by processor 204, cause processor 204 to perform the operations encoded therein.

Processor 204 may include, but is not limited to, a general purpose central processing unit (CPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer-readable medium including, without limitation, a storage device and/or a memory device. Such instructions, when executed by processor 204, cause processor 204 to perform at least a portion of the methods described herein. The above examples are exemplary only, and thus are not intended to limit in any way the definition and/or meaning of the term processor.

Memory device 206, as described herein, is one or more devices that enable information such as executable instructions and/or other data to be stored and retrieved. Memory device 206 may include one or more computer-readable media, such as, without limitation, dynamic random access memory (DRAM), static random access memory (SRAM), a solid state disk, and/or a hard disk. Memory device 206 may be configured to store, without limitation, maintenance event log, diagnostic entries, fault messages, and/or any other type of data suitable for use with the methods and systems described herein.

In the illustrated embodiment, computing device 200 includes a presentation interface 208 that is coupled to processor 204. Presentation interface 208 outputs (e.g., display, print, and/or otherwise output) information such as, but not limited to, installation data, configuration data, test data, error messages, and/or any other type of data to a user 214. For example, presentation interface 208 may include a display adapter (not shown in FIG. 2) that is coupled to a display device, such as a cathode ray tube (CRT), a liquid crystal display (LCD), a light-emitting diode (LED) display, an organic LED (OLED) display, and/or an "electronic ink" display. In some implementations, presentation interface 208 includes more than one display device. In addition, or in the alternative, presentation interface 208 may include a printer. In other embodiments, computing device does not include presentation interface 208 and/or is not coupled to a display device.

In the exemplary embodiment, computing device 200 includes an input interface 210 that receives input from user 214. For example, input interface 210 may be configured to receive selections, requests, credentials, and/or any other type of inputs from user 214 suitable for use with the methods and systems described herein. In the exemplary implementation, input interface 210 is coupled to processor 204 and may include, for example, a keyboard, a card reader (e.g., a smartcard reader), a pointing device, a mouse, a stylus, a touch sensitive panel (e.g., a touch pad or a touch screen), a gyroscope, an accelerometer, a position detector, and/or an audio input interface. A single component, such as a touch screen, may function as both a display device of presentation interface 208 and as input interface 210. In other embodiments, computing device does not include input interface 210 or includes an input interface for receiving instructions from another computing device 200.

In the exemplary embodiment, computing device 200 includes a communication interface 212 coupled to memory 206 and/or processor 204. Communication interface 212 is coupled in communication with one or more remote device, such as another computing device 200, sensor assembly 104, etc. Communication interface 212 may include, without limitation, a wired network adapter, a wireless network adapter, an input/output port, analog to digital input/output port, and a mobile telecommunications adapter. Although a single communication interface 212 is shown in FIG. 2, in other embodiments, computing device 200 includes more than one communication interface 212.

Instructions for operating systems and applications are located in a functional form on non-transitory memory 206 for execution by processor 204 to perform one or more of the processes described herein. These instructions in the different implementations may be embodied on different physical or tangible computer-readable media, such as memory 206 or another memory, such as a computer-readable media 218, which may include, without limitation, a flash drive, CD-ROM, thumb drive, etc. Further, instructions are located in a functional form on non-transitory computer-readable media 218, which may include, without limitation, a flash drive, CD-ROM, thumb drive, etc. Computer-readable media 218 is selectively insertable and/or removable from computing device 200 to permit access and/or execution by processor 204. In one example, computer-readable media 218 includes an optical or magnetic disc that is inserted or placed into a CD/DVD drive or other device associated with memory 206 and/or processor 204. In some instances, computer-readable media 218 may not be removable.

Figure 3:
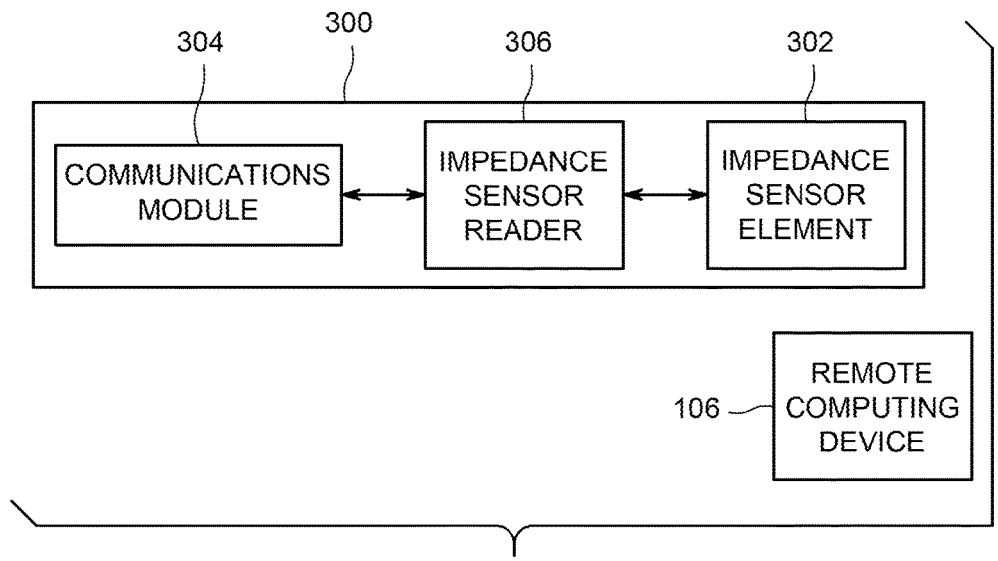
FIGS. 3 and 4 are block diagrams of exemplary sensor assemblies for use in the network shown in FIG. 1.
Figure 4:
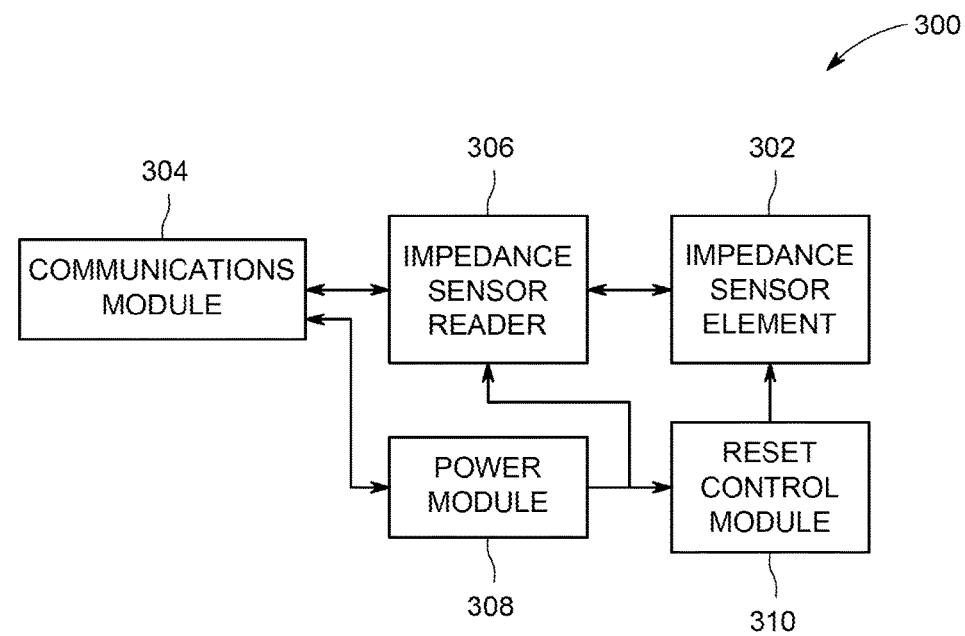

FIGS. 3 and 4 is a block diagram of an exemplary sensor assembly 300 that may be used as sensor assembly 104 in sensor network 100 (both shown in FIG. 1). Sensor assembly 300 includes an impedance sensor element 302, an impedance sensor reader 306, and a communications module 304. Sensor assembly 300 communicates with a remote computing device, such as remote computing device 106.

FIG. 4 is a block diagram of another exemplary sensor assembly 300 that may be used as sensor assembly 104 in sensor network 100 (both shown in FIG. 1). Sensor assembly 300 includes an impedance sensor element 302, a communications module 304, an impedance sensor reader 306, a power module 308, and a reset control module 310.

In some embodiments, the communications module 304 includes a radio, a radio frequency (RF) front end, and an antenna assembly (not shown). The radio is configured for communication according to one or multiple wireless protocols. The radio is also configured to packetize of sensor data for transmission. The RF front end performs filtering and controls the reception and transmission of wireless signals. The antenna assembly includes one or more antennas configured to transform signals to electromagnetic signals for sending and receiving data wirelessly.

In an example, a portion of computing may be performed in a remote computing device and a portion of computing may be performed in an impedance sensor reader. In another example, computing may be performed in an impedance sensor reader.

In the exemplary embodiment, impedance sensor element 302 is a resonant sensor element, such as a passive radio frequency identification (RFID) sensor element. In other embodiments, impedance sensor elements 302 include inductor-capacitor-resistor (LCR) sensors, thickness shear mode (TSM) resonator sensors, acoustic wave (AW) sensors, surface acoustic wave (SAW) sensors, tuning fork sensors, or split ring resonator (SRR) sensors. The impedance of impedance sensor element 302 is changed by the presence of analytes in the environment (such as industrial fluid) around resonant sensor element 302. As used herein, the term "analyte" refers to a substance that includes any desirable measured environmental parameter. As described herein, sensor assembly 300 determines the changed impedance of impedance sensor element 302 to determine the amount of a particular analyte present in the environment. Moreover, in some embodiments, impedance sensor element 302 is differently responsive to different analytes, and the amount of more than one analyte present is determined by sensor assembly 300.

Communications module 304 is configured to communicate with a remote device, such as remote computing device 106 (shown in FIG. 1) or another sensor assembly 300. In the exemplary sensor assembly 300, communications module 304 is a wireless communications module configured for wireless communication between sensor assembly 300 and one or more remote device. In some embodiments, communications module 304 is configured for communication with both remote computing device 106 and other sensor assemblies 104. In some embodiments of sensor network 100, only one sensor assembly 104, 300 is configured to communicate, using communications module 304, with both remote computing device 106 and other sensor assemblies 104, 300. In such embodiments, sensor network 100 is configured in a mesh network and all other sensor assemblies 104, 300 are configured to communicate, using communications module 304, only with other sensor assemblies 104, 300. In other mesh network embodiments of sensor network 100, more than one sensor assembly 104, 300 is configured to communicate, using communications module 304, with both remote computing device 106 and other sensor assemblies 104, 300.

Impedance sensor reader 306 is coupled to impedance sensor element 302 and configured to detect the impedance of impedance sensor element 302. Impedance sensor reader 306 includes a synthesizer and a detector (neither shown in FIG. 4). The synthesizer is configured to output to the impedance sensor element 302 the excitation signal having known values for a plurality of signal characteristics, such as amplitude, phase, and frequency. The synthesizer is configured to generate the excitation signal based on a plurality of DDS coefficients received from remote computing device 106 through the communications module 304. The detector is configured to detect a response of impedance sensor element 302 to the excitation signal and determine the impedance of the impedance sensor element 302 based on the response. To get an accurate estimate of the impedance, the detection electronics may track the amplitude and the phase of the response.

Power module 308 provides the power for operation of sensor assembly 300. Power module 308 includes a power source and a power module controller (neither shown in FIG. 4). Sensor assembly 300 is self-powered and the power source includes a photovoltaic (PV) power source and an energy storage device in the exemplary embodiment. In other embodiments, the power source includes other miniaturized power sources such as ultrasonic receivers integrated with the sensor node which can be powered from the sensor hub with a focused ultrasonic beam, or any other suitable localized power source. In some embodiments, the power source is an energy harvesting source based on nonlimiting known types of energy (e.g. solar, photonic, thermal, mechanical, vibrational, ambient radio-frequency). The energy storage device is a battery, a capacitor, a supercapacitor, any other suitable energy storage device or combination of energy storage devices. In still other embodiments, the power source is a remote power source, such as a utility grid. In the exemplary embodiments, sensor assemblies 300 are self-powered and each sensor assembly includes its own power source. In other embodiments, a power source, such as an array of PV modules, acts as the power source for more than one sensor assembly 300. The power module controller controls operation of power module 308 to produce, store, and deliver power appropriately. In the exemplary embodiment, the power module controller monitors the charging and discharging rate of the energy storage device and coordinates power saving operations. The power module also controls, when applicable, the power source and the power conversion processes. For example, when the power source includes a PV module, the power module provides maximum power point tracking (MPPT) to attempt to maximize the power produced by the PV module.

Reset control module 310 is configured to use power from power module 308 to reset impedance sensor element 302. As described above, the impedance of impedance sensor element 302 changes in the presence of gases in the environment due to adsorption of the gas on the impedance sensor element 302. Reset control module 310 periodically provides a relatively large current of electricity to impedance sensor element 302. The large electrical current through the resistive impedance sensor element 302 generates heat that increases the temperature of impedance sensor element 302 and causes adsorbed gases to be released. Ideally, the reset will release all adsorbed gas and return impedance sensor element 302 to its initial impedance. In some embodiments, reset control module 310 compares the impedance of impedance sensor element 302 to a reference impedance at a known frequency to determine whether or not the reset was successful. If the difference between the reference impedance and the post-reset impedance of impedance sensor element 302 exceeds a threshold, for example and without limitation, more than 1%, more than 5%, or more than 10%, reset control module 310 reattempts to reset impedance sensor element 302. Reset control module includes instruction to attempt to save power and help attempt to minimize power consumption of sensor assembly 300. For example, because a reset requires a relatively large electrical current, reset control module 310 is configured in some embodiments to delay initiating a reset until a predetermined amount of power is being produced or until a predetermined charge status of the energy storage device is met. In some embodiments, the impedance sensor reader includes a processor to compute response of the impedance sensor element.

Figure 5:
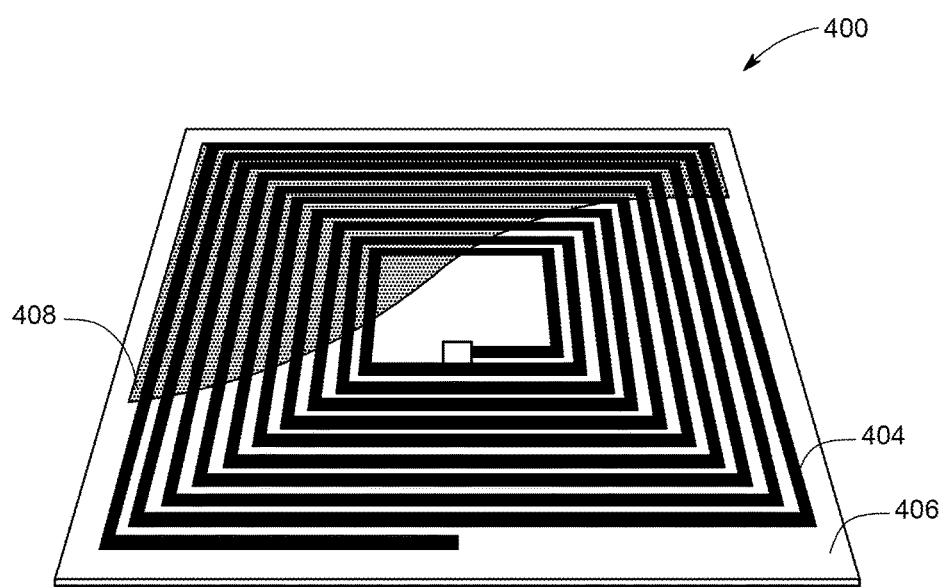
FIG. 5 is an exemplary impedance sensor element for use in the sensor assemblies shown in FIGS. 3 and 4.
Figure 6:
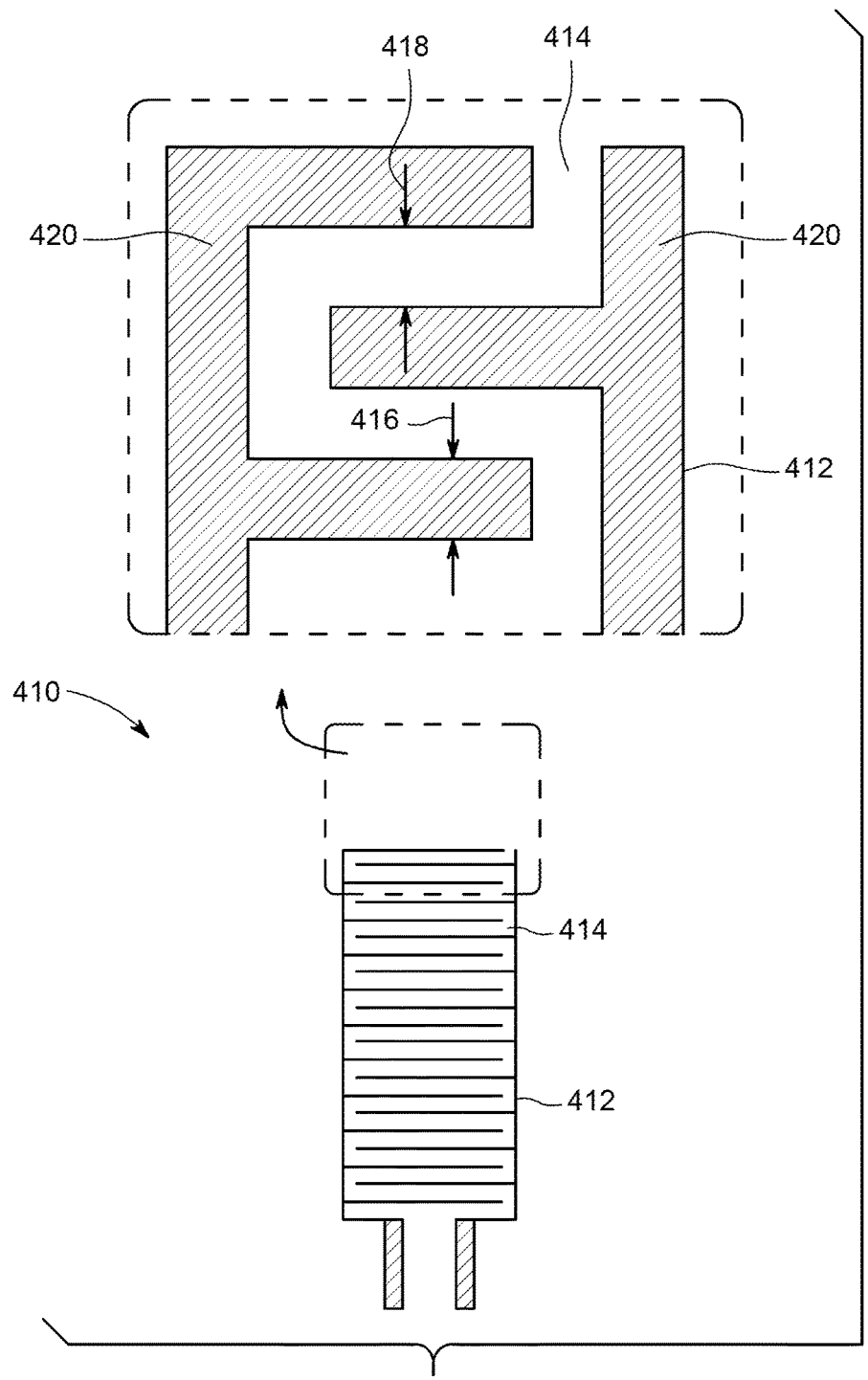
FIG. 6 is another exemplary impedance sensor element for use in the sensor assemblies shown in FIGS. 3 and 4 and including an interdigitated electrode structure disposed on a substrate.

FIGS. 5 and 6 illustrate non-limiting examples of designs of electrodes of an impedance sensor element.

FIG. 5 is an example multivariable sensor element 400 for use as impedance sensor element 302 (shown in FIGS. 3 and 4). Sensor element 400 is a passive RFID sensor with an antenna circuit 404 disposed on a substrate 406. Antenna circuit 404 is covered at least partially by a sensing film 408.

The RFID sensor is an RFID tag with an added sensing function. Antenna circuit 404 of the RFID tag performs sensing functions by changing its impedance parameters as a function of environmental changes. The antenna circuit 404 is the sensing region. The determination of environmental changes is performed by analysis of impedance of multivariable resonant sensor element 400. The material changes in the resonant sensor element 400, and particularly changes to antenna circuit 404, upon exposure to an analyte are measured. Dielectric, dimensional, charge transfer, and other changes of materials properties may be detected by the changes in the resonant properties of resonant sensor element 400.

Sensing film 408 is disposed on antenna circuit 404 to alter the impedance response of multivariable resonant sensor element 400. Depositing sensing film 408 onto antenna circuit 404 creates an RFID chemical, biological, or physical sensors. In another approach, a complementary sensor may be attached across an antenna and an optional memory chip. The complementary sensor may be used to alter sensor impedance response. Non-limiting examples of such sensors are described in U.S. Pat. No. 7,911,345 entitled "Methods and systems for calibration of RFID sensors". As used herein the term "sensing materials and sensing films" includes, but is not limited to, materials deposited onto the RFID sensor to perform the function of predictably and reproducibly affecting the complex impedance sensor response upon interaction with the environment. For example, a conducting polymer such as polyaniline changes its conductivity upon exposure to solutions of different pH. When such a polyaniline film is deposited onto multivariable resonant sensor element 400, the complex impedance sensor response changes as a function of pH. Thus, such an RFID sensor works as a pH sensor. When such a polyaniline film is deposited onto the RFID sensor for detection in gas phase, the complex impedance sensor response also changes upon exposure to basic (for example, NH3) or acidic (for example HCl) gases. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, metal-oxide, cryptophane, metal-organic framework, carbon nanoparticles, graphene, molybdenum disulfide, electrospun polymer nanofibers, electrospun inorganic nanofibers, electrospun composite nanofibers, and any other sensor material. In order to prevent the material in the sensor film from leaking into the liquid environment, the sensor materials are attached to the sensor surface using standard techniques, such as, without limitation, covalent bonding, and electrostatic bonding. Additional sensors, sensor assemblies, and impedance measurement techniques capable of being used in sensor assemblies of the present disclosure are described in U.S. Pat. App. Pub. No. 2014/0095102 entitled "Systems and Methods of Monitoring Sensors", and U.S. Pat. App. Pub. No. 2014/0091811 entitled "Systems and Methods of Monitoring Sensors".

FIG. 6 is an example of impedance sensor element 410 for use as impedance sensor element 302 (shown in FIGS. 3 and 4). Sensor element 410 includes an interdigital (interdigitated) electrode structure 412 disposed on a substrate 414. The interdigitated electrode structure 412 is the sensing region. The interdigitated electrode structure 412 is covered at least partially by a sensing film (not shown). This interdigital electrode structure has an electrode width 416 and an electrode spacing 418 (also referred to as a gap) between electrodes 420. The spacing between electrodes 420 can be the same or different in different directions. Nonlimiting examples of a sensing region are interdigitated two-electrode structures with the electrode width and the spacing between electrodes in the range from 1 nanometer and 1 centimeter and sensing area in the range from 1 square micrometer to 10 square centimeters. In an exemplary embodiment, the electrode width 416 and electrode spacing 418 are both about 0.45 mm.

Other suitable interdigitated electrodes include electrode structures with variable electrode width and spacing, tapered electrodes, circular electrodes, and others known in the art. Although two electrodes 420 are shown, other embodiments include four electrodes 420 or more than four electrodes 420.

Figure 7:
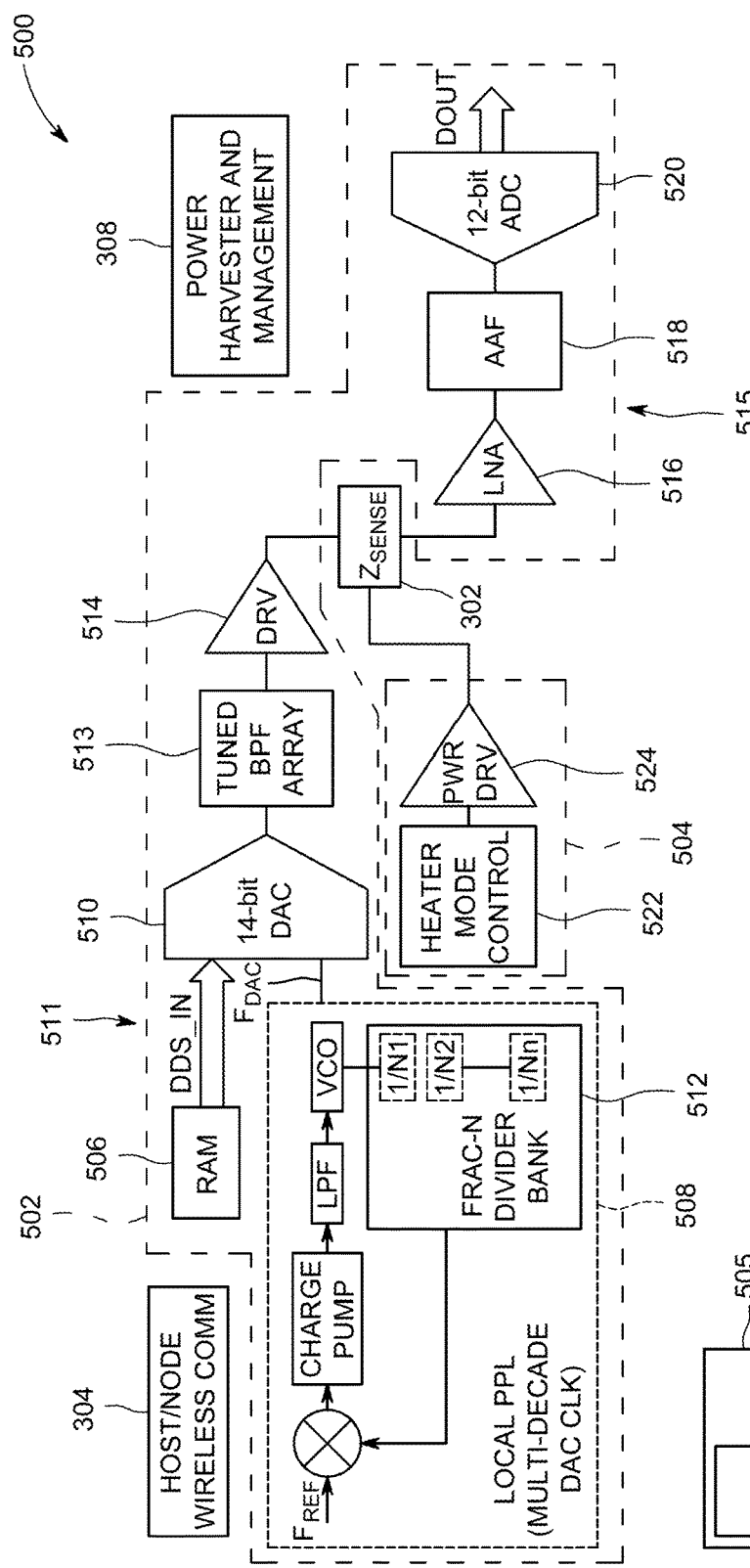
FIG. 7 is an exemplary sensor assembly for use in the network shown in FIG. 1.

FIG. 7 is a block diagram of an exemplary embodiment of a sensor assembly 500 suitable for use as sensor assembly 300 (shown in FIGS. 3 and 4). Sensor assembly 500 includes communications module 304 (shown in FIGS. 3 and 4), an impedance sensor 502, impedance sensor element 302 (shown in FIG. 1), power module 308 (shown in FIGS. 3 and 4), a reset control module 504, and a controller 505.

Controller 505 controls overall operation of sensor assembly 500. Controller 505 includes a processor 507 and a memory device 509. In other embodiments, controller is an analog controller or an analog and digital controller. Although illustrated as a discrete component, controller 505 is a description of control functions and aspects of sensor assembly 500 and may actually be distributed about and performed by one or more other components of assembly 500.

Impedance sensor reader 502 includes a synthesizer 511 and a detector 515. Synthesizer 511 includes a random access memory (RAM) memory device 506, a local phase locked loop (PLL) 508, a digital-to-analog converter (DAC) 510, a tuned band pass filter array (BPF) 513, and a driver (DRV) 514. DDS coefficients generated by remote computing device 106 (shown in FIG. 1) and received by assembly 500 through communications module 304 are stored in memory device 506. In some embodiments, calibration coefficients for analog-to-digital conversion (ADC) are also stored in memory device 506. In some embodiments, memory device 506 stores other data and/or instructions for impedance sensor 502 or any other component of sensor assembly 500.

To span multiple decades of frequency, PLL 508 generates a multi-decade clock reference for DAC 510. To reduce the power consumption in the reference generation, PLL 508 outputs a clock signal with relatively low jitter, but without particularly low total harmonic distortion (THD). The reference clock is scaled by PLL 508 to allow several decades to be scanned with the same DDS coefficients. The clock is generated using a low power digital divider network 512 of fractional and/or integer dividers. In some embodiments, multiple crystal oscillators are used in PLL 508 instead of divider network 512. In still other embodiments a clock cleaner PLL is used to scale the reference clock. PLL 508 includes a voltage controlled oscillator (VCO), a mixer, charge pump and a Low pass loop filter (LPF) to reject high frequency ripple in the mixer, charge pump response. The VCO is a ring oscillator with calibration coefficients specified along with the DDS coefficients. In other embodiments, the VCO is a digitally controlled oscillator, for ease of calibration.

The DDS coefficients stored in memory device 506 and the clock signal generated by PLL 510 are used as inputs to DAC 510. DAC 510 uses the DDS coefficients and the clock signals to synthesize the excitation signal with known signal characteristics. The output of DAC 510 is filtered by a tuned band pass filter array 513. A driver 514 supplies the filtered excitation signal to impedance sensor element 302. Generating both the DAC calibration and the DDS coefficients at a host remotely from the sensor nodes, reduces the active power dissipation of the DAC and filter circuitry. The response of impedance sensor element 302 to the excitation signal is received detector 515. Detector 515 includes a low noise amplifier (LNA) 516, which amplifies the signal and outputs the amplified response to a filter 518. The amplified and filtered response is provided to an analog-to-digital converter (ADC) 520. An Anti-Aliasing Filter (AAF) may be used prior to the ADC in some embodiments. Some embodiments include a mixer (not shown) between impedance sensor element 302 and ADC 520 to reduce ADC sample rates. The digitized data is output from impedance sensor 502 for storage in memory device 509. In some embodiments, the data is stored in memory device 506. In the exemplary embodiment, the raw output data is stored in memory device 509 for transmission to remote computing device 106. In other embodiments, averaging functions are applied by processor 507 to the raw data to compress the amount of data that will need to be transmitted from sensor assembly 500 to remote computing device 106. In some embodiments, processor 507 calculates an impedance of sensor element 302 based on the raw data and stores the results of the calculation for transmission to remote computing device 106.

Reset control module 504 includes a controller 522 and a power driver 524. Controller 522 determines when to reset resonant antenna element 302. Controller 522 uses power driver 524 to apply a relatively large electric current from power module 308 to resonant antenna element 302 to reset resonant antenna element 302 as described above.

Figure 8:
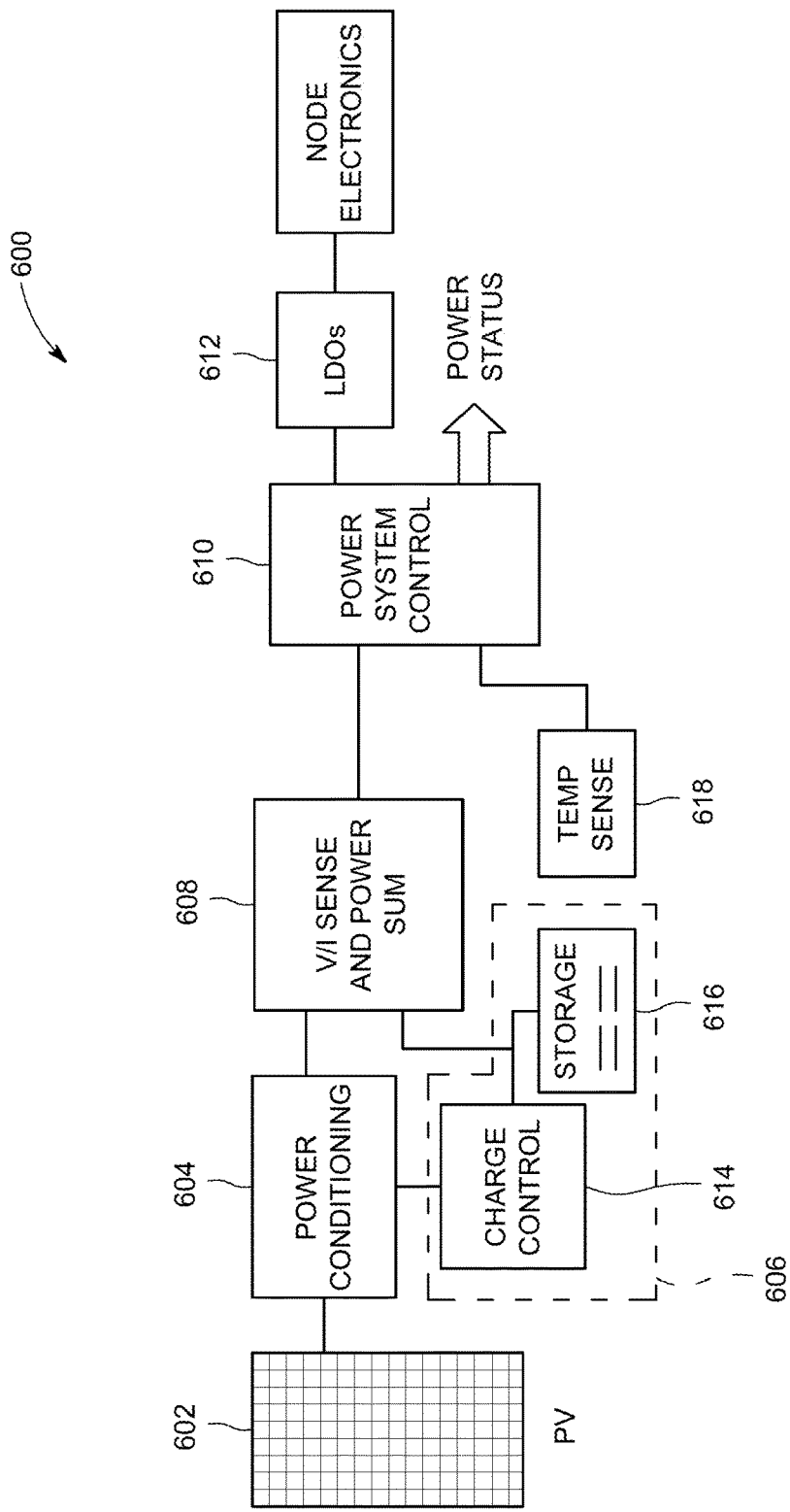
FIG. 8 is an exemplary power module for use in the sensor assembly shown in FIG. 7.

FIG. 8 is a block diagram of an exemplary embodiment of a power module 600 suitable for use as power module 308 (shown in FIGS. 3 and 4). Power module 600 includes a PV panel 602, a power conditioner 604, a storage system 606, a power sensor 608, a control system 610, and an output regulator 612.

PV panel 602 produces a direct current (DC) output in response to light shining on the panel. The output is provided to power conditioner 604 that conditions the power output to provide an output with the desired characteristics, such as the desired voltage. Storage system 606 is connected to the output of power conditioner 604. A charge controller 614 charges energy storage device 616 to store energy for use when PV panel 600 is not producing enough power for operation of sensor assembly 500 (shown in FIG. 7), such as at night or when significant clouds are present. Power sensor 608 monitors the voltage (V) and current (I) output from conditioner 604. When the output is insufficient for operation of sensor assembly 500, power sensor pulls additional power from energy storage device 616.

Control system 610 is a power system controller that controls and directs power module 600. Control system 610 monitors both the charging and discharging rates of the storage device 616 and prevents storage system 606 from charging energy storage device 616 when the power output by PV panel 602 is insufficient for the current operating needs of sensor assembly 500. Control system 610 also monitors residual power available and co-ordinates various power saving methods, such as scaling the excitation power for DAC 510, the power of amplifier 516, and the scanning resolution of ADC 520 (all shown in FIG. 7) according to the amount of power available. Such methods save power at the cost of less accurate impedance measurements. A temperature sensor 618 monitors the temperature of the power module and provides the result to control system 610 so that control system 610 may take appropriate action if excessive temperatures occur.

The produced electric power of power module 600 is output from module 600 using output regulators 612. In the exemplary embodiment regulators 612 are low-drop out regulators (LDOs). In other embodiments, output regulators 612 may be any suitable regulator.

Figure 9:
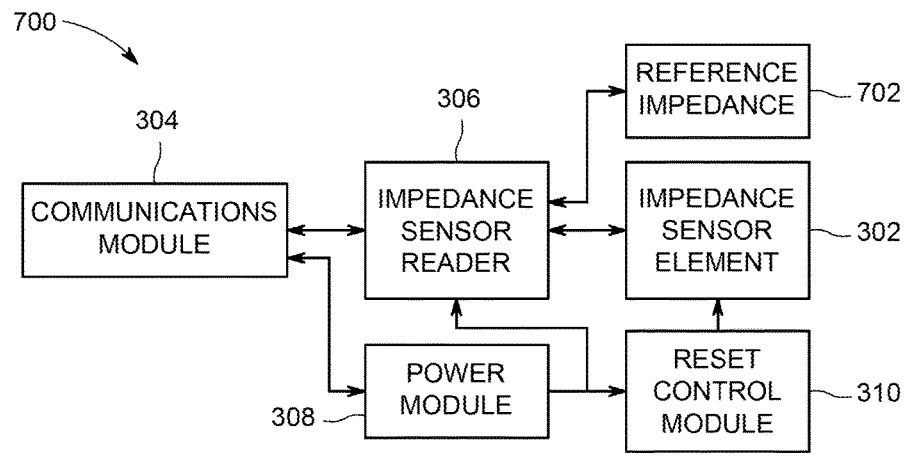
FIG. 9 is another exemplary sensor assembly for use in the network shown in FIG. 1.

FIG. 9 is a block diagram of another embodiment of an exemplary sensor assembly 700 that may be used as sensor assembly 104 in sensor network 100 (both shown in FIG. 1). Sensor assembly 700 is similar to sensor assembly 300 (shown in FIGS. 3 and 4) and similar reference numerals are used to indicate similar components. Sensor assembly 700 compresses the dynamic range of the impedance scanning to further reduce power requirements of sensor assembly 700. Specifically, sensor assembly 700 includes a reference impedance 702. Sensor assembly 700 rather than determining an absolute impedance of impedance sensor element 302 (shown in FIGS. 3 and 4), sensor assembly 700 differentially senses the impedance variation between sensor element 302 and reference impedance 702. This reduces the requirement of the DAC and ADC used in sensor assembly 700. Moreover the scan range is narrowed by coarse-fine scanning to compress the number of points in the scanned spectrum.

Figure 10:
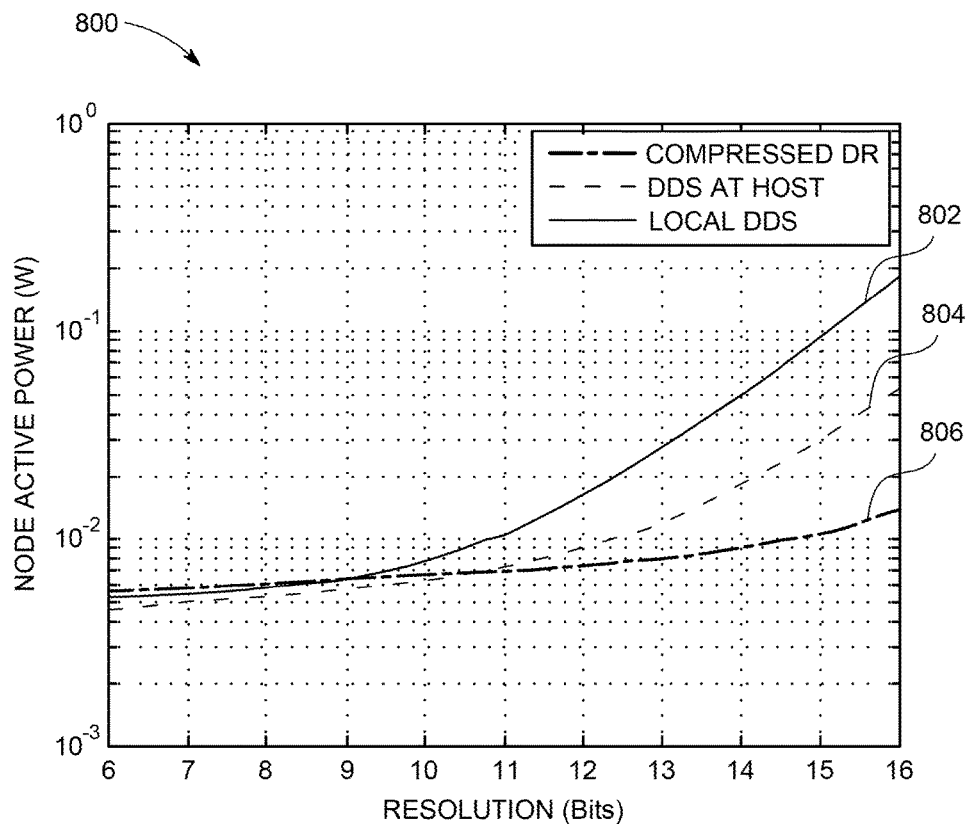
FIG. 10 is a graph of simulated power requirements as a function of resolution for three exemplary sensor assemblies.

FIG. 10 is a graph 800 of power requirements of various sensor assemblies that may be needed for use in sensor network 100 (shown in FIG. 1). The graph 800 charts the power requirements (in Watts) on a logarithmic scale for three different sensor assemblies as a function of resolution of measurements of response of the impedance sensor element that is between 6 bits and 16 bits. Trace 802 represents the power requirements of a sensor assembly similar to assemblies 104 (shown in FIG. 1), 300 (shown in FIGS. 3 and 4), and 500 (shown in FIG. 7), but which determines its own DDS coefficients (local DDS determination). Above a resolution of about nine bits, this sensor assembly has the greatest power requirements due because of the processing intensive calculation of DDS coefficients. Trace 804 represents the power requirements of a sensor assembly similar to assemblies 104, 300, and 500, which receives DDS coefficients from a remote computing device (referred to sometimes as a host computing device). Trace 806 represents the power requirements of a sensor assembly similar to assembly 700 (shown in FIG. 7), which receives DDS coefficients from a remote computing device and performs dynamic range (DR) compression. Below a resolution of about nine bits, all three traces 802, 804, 806 have similar power requirements because of relatively fixed minimum power requirements of the assemblies.

Sensor elements as described herein may be utilized, for example, for methane detection based a conventional SnO2 metal oxide composition. An example sensor element was built and operated in a resonant mode with measurements performed using built-in-house impedance sensor reader. This sensor operation provides multivariable response of the sensor. The sensor was exposed to different concentrations of methane such as 0, 111, 222, 444, 666, and 888 ppm in air to calibrate the sensor. The sensor used a transfer function of:

$$CH_4 \text{ concentration (ppm)} = A_0 + A_1 * SO_1 + A_2 * SO_2 + A_3 * SO_3 + A_4 * SO_4$$

where $SO_1$, $SO_2$, $SO_3$, and $SO_4$ are examples of outputs of a single multivariable sensor and $A_0$, $A_1$, $A_2$, $A_3$, and $A_4$ are examples of coefficients of the transfer function.

Nonlimiting examples of outputs of a single multivariable sensor may be the frequency of the maximum of the real part of the complex impedance (Fp, resonance peak position), magnitude of the real part of the complex impedance (Zp, peak height), zero-reactance frequency (Fz, frequency at which the imaginary portion of impedance is zero), resonant frequency of the imaginary part of the complex impedance (F1), and anti-resonant frequency of the imaginary part of the complex impedance (F2), signal magnitude (Z1) at the resonant frequency of the imaginary part of the complex impedance (F1), and signal magnitude (Z2) at the anti-resonant frequency of the imaginary part of the complex impedance (F2). Other parameters may be measured using the entire complex impedance spectra, for example, quality factor of resonance, phase angle, and magnitude of impedance. Multivariable response spectral parameters are described in U.S. Pat. No. 7,911,345 entitled "Methods and systems for calibration of RFID sensors", U.S. Pat. App. Pub. No. 2014/0095102 entitled "Systems and Methods of Monitoring Sensors", and U.S. Pat. App. Pub. No. 2014/0091811 entitled "Systems and Methods of Monitoring Sensors".

Figure 11:
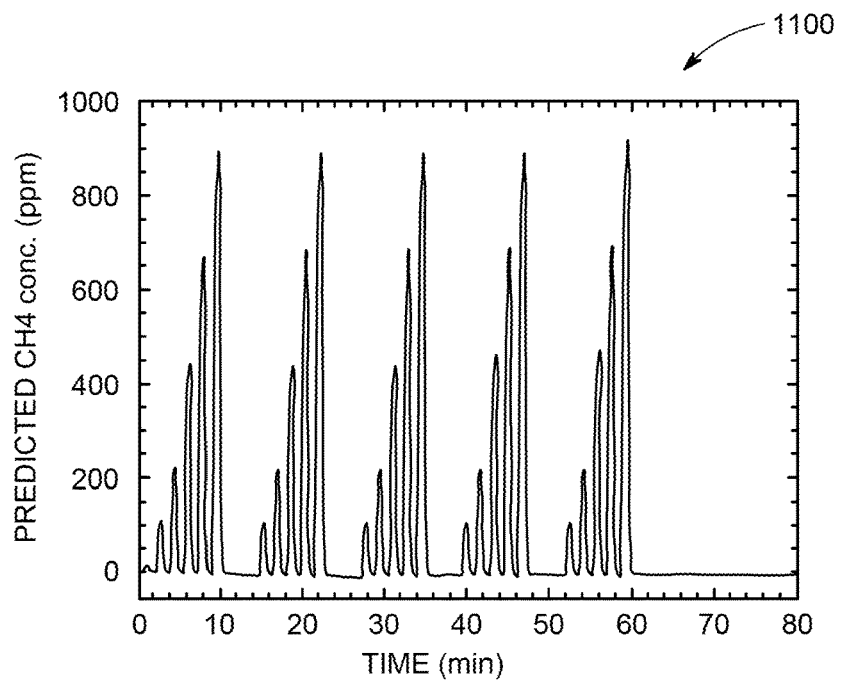
FIG. 11 is a graph of the result of applying a developed transfer function to display methane concentrations as measured with an exemplary methane sensor.

FIG. 11 is a graph 1100 of the result of applying the developed transfer function to display methane concentrations as measured with the methane sensor. These predicted methane concentrations are depicted in FIG. 11 as a function of time, illustrating five replicate sets of measurements of actual methane concentrations of 0, 111, 222, 444, 666, and 888 ppm in air. Each set of measurements of actual methane concentrations took about twelve and one half minutes, performing all five sets in about sixty-two and one half minutes. Thus, FIG. 11 shows the operation of the sensor calibrated for methane detection.

Figure 12:
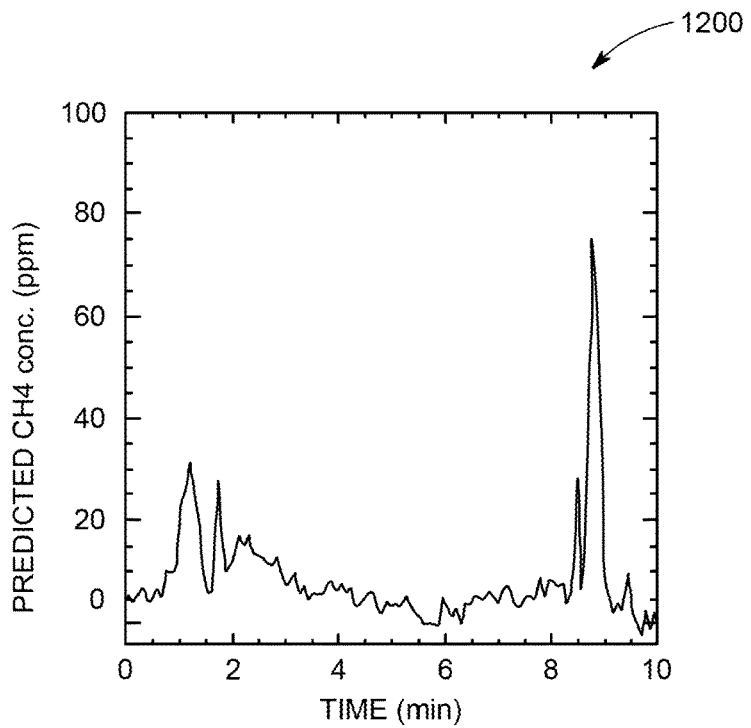
FIG. 12 is a graph of the result of outdoors stand-off detection of methane leaks with the calibrated exemplary methane sensor during about 10 minutes time of measurements.

The calibrated sensor was further utilized to perform measurements of methane leaks outdoors. A model leak was generated using a methane gas tank with 1% methane in air, having the tank to release its gas composition through two-stage regulator and a valve, and detecting the gas leaks with the sensor at different distances from the gas tank. FIG. 12 is a graph 1200 of the results of this outdoors stand-off detection of methane leaks with the calibrated sensor during about 10 minutes time of measurements. The first leak was detected at about one to two minutes as indicated by the methane concentration increase as detected by the sensor. At this time, the distance between the sensor and the source of methane leak was about five meters and the wind was directed from the leak to the sensor. Next, the leak was stopped by closing the valve and the distance between the sensor and the source of methane leak was decreased to about three and one half meters. Upon opening the valve, the sensor detected the methane concentration increase at the time of about eight and one half to nine and one half minutes as indicated by the methane concentration increase as detected by the sensor with the wind directed again from the leak to the sensor. Thus, FIG. 12 shows the operation of the sensor calibrated for methane detection for the stand-off detection of methane leaks outdoors.

Self-powered sensor nodes, such as sensor assemblies 104, 300, 500, and 700, offload DDS coefficient calculation to a remote computing device, resulting in lower power consumption as compared to some known sensor nodes. Moreover, power requirements are further reduced through implementation of additional power saving techniques, such as pre-distorting DDS coefficients, using a local clock cleaner PLL, use of a reference impedance, compression of data, and use of multiple lower power scans. The resulting lower power consumption permits the sensor nodes to be self-powered by a reasonably sized, local resource, such as a small PV panel and a rechargeable energy storage device. The reasonable size and self-powering of the sensor nodes allows them to be used in remote, hostile, and/or unpowered locations at which many known sensors could not be used.

An exemplary technical effect of the methods, systems, and apparatus described herein includes at least one of: (a) reducing the computational load on a sensor node through calculation of DDS coefficients at remote computing device; (b) reducing the power requirements of a sensor node; (c) permitting a sensor node to be self-powered by a local power source; (d) increasing the efficiency of sensor nodes; and (e) extending the environments in which sensor nodes are useable.

Exemplary embodiments of the systems and methods are described above in detail. The systems and methods are not limited to the specific embodiments described herein, but rather, components of the systems and/or steps of the methods may be utilized independently and separately from other components and/or steps described herein. For example, the system may also be used in combination with other apparatus, systems, and methods, and is not limited to practice with only the system as described herein. Rather, the exemplary embodiment can be implemented and utilized in connection with many other applications. Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A sensor assembly comprising:
   an impedance sensor element;
   a communications module configured to communicate with a remote computing device;
   an impedance sensor reader coupled to said impedance sensor element and comprising:
     a synthesizer configured to output an excitation signal having known signal characteristics over a range of frequencies, said synthesizer configured to generate the excitation signal based on a plurality of direct digital synthesizer (DDS) coefficients received from the remote computing device through said communications module; and
     a detector coupled to said impedance sensor element and configured to detect a response of said impedance sensor element to the excitation signal and determine an impedance of said impedance sensor element;
   a power harvesting and management unit to allow for stand-alone operation of said sensor assembly; and
   a reset control module configured to reset said impedance sensor element to an initial impedance and release adsorbed gases from said impedance sensor element, wherein resetting said impedance sensor element is based on the impedance of said impedance sensor element exceeding a threshold value.

2. The sensor assembly according to claim 1, wherein said detector is configured to determine impedance changes of said impedance sensor element in response to one or more components of a fluid affecting the impedance sensor element, and wherein the fluid is an industrial fluid.

3. The sensor assembly according to claim 2, wherein the plurality of signal characteristics of the excitation signal includes the amplitude, frequency, and phase of the excitation signal.

4. The sensor assembly according to claim 1, wherein said synthesizer comprises:
   a memory device for storing the plurality of DDS coefficients received from the remote computing device through said communications module; and
   a digital/analog converter (DAC) configured to generate the excitation signal based on the plurality of DDS coefficients stored in said memory device and a clock signal.

5. The sensor assembly according to claim 4, wherein said synthesizer further comprises a one of a phase locked loop (PLL) and a low jitter clock oscillator configured to generate the clock signal.

6. The sensor assembly according to claim 1, wherein said power harvesting and management unit is configured to provide power to said communications module and said impedance sensor, said power harvesting and management unit comprising a local power source, an energy storage device, and a power module controller configured to monitor power storage and calculate available power to permit provision of sufficient power for impedance measurement and communication.

7. The sensor assembly according to claim 6, wherein said power module controller is configured to selectively prevent operation of one or both of the communications module and the impedance sensor reader if it determines there is insufficient power available from the power module.

8. The sensor assembly according to claim 1, wherein said communications module comprises:
   a radio configured for communication according to at least one wireless protocol, and configured to perform packetization of sensor data;
   a radio frequency (RF) front end configured to perform filtering and to control the reception and transmission of wireless signals; and
   an antenna assembly including at least one antenna to transform RF signals to electromagnetic signals for sending and receiving data wirelessly.

9. The sensor assembly according to claim 1, wherein said reset control module is configured to:
   determine an approximate impedance of said impedance sensor element;
   compare the determined approximate impedance to the reference impedance at a known frequency; and
   determine a magnitude of the current to be applied to said impedance sensor element based at least in part on a difference of the determined approximate impedance to the reference impedance exceeding the threshold value.

10. The sensor assembly according to claim 1, wherein said sensor assembly is not configured to calculate any DDS coefficients.

11. The sensor assembly according to claim 1 further comprising a reference impedance coupled to said impedance sensor, wherein said impedance sensor is configured to determine the impedance of said impedance sensor element by determining a difference between a response of said impedance sensor element to the excitation signal and a response of said reference impedance to the excitation signal.

12. The sensor assembly according to claim 1 where the sensor assembly is a part of a consumer electronics system.

13. A method of operating a sensor node including an impedance sensor element, said method comprising:
   receiving, by the sensor node, a plurality of direct digital synthesizer (DDS) coefficients from a remote computing device;
   storing, by the sensor node, the plurality of DDS coefficients in a memory device;
   generating, by the sensor node, an excitation signal based on the plurality of DDS coefficients and a clock signal;
   determining, by the sensor node, an impedance of the impedance sensor element based at least in part on the response of the impedance sensor element to the excitation signal;
   determining, by a reset control module configured in the sensor node, the impedance of the impedance sensor element exceeds a threshold value associated with a reference impedance at a known frequency;
   resetting, by the reset control module, the impedance sensor element to an initial impedance and releasing absorbed gases from the impedance sensor element; and
   transmitting the determined impedance of the impedance sensor element to the remote computing device based on resetting the impedance sensor element.

14. The method according to claim 13, wherein said receiving a plurality of DDS coefficients from a remote computing device comprises receiving a plurality of DDS coefficients pre-distorted by the remote computing device based on at least one operational characteristic of the sensor node.

* * * * *